May 16, 1967 E. S. BOERNER Plant Pat. 2,739
CHRYSANTHEMUM PLANT
Filed May 9, 1966
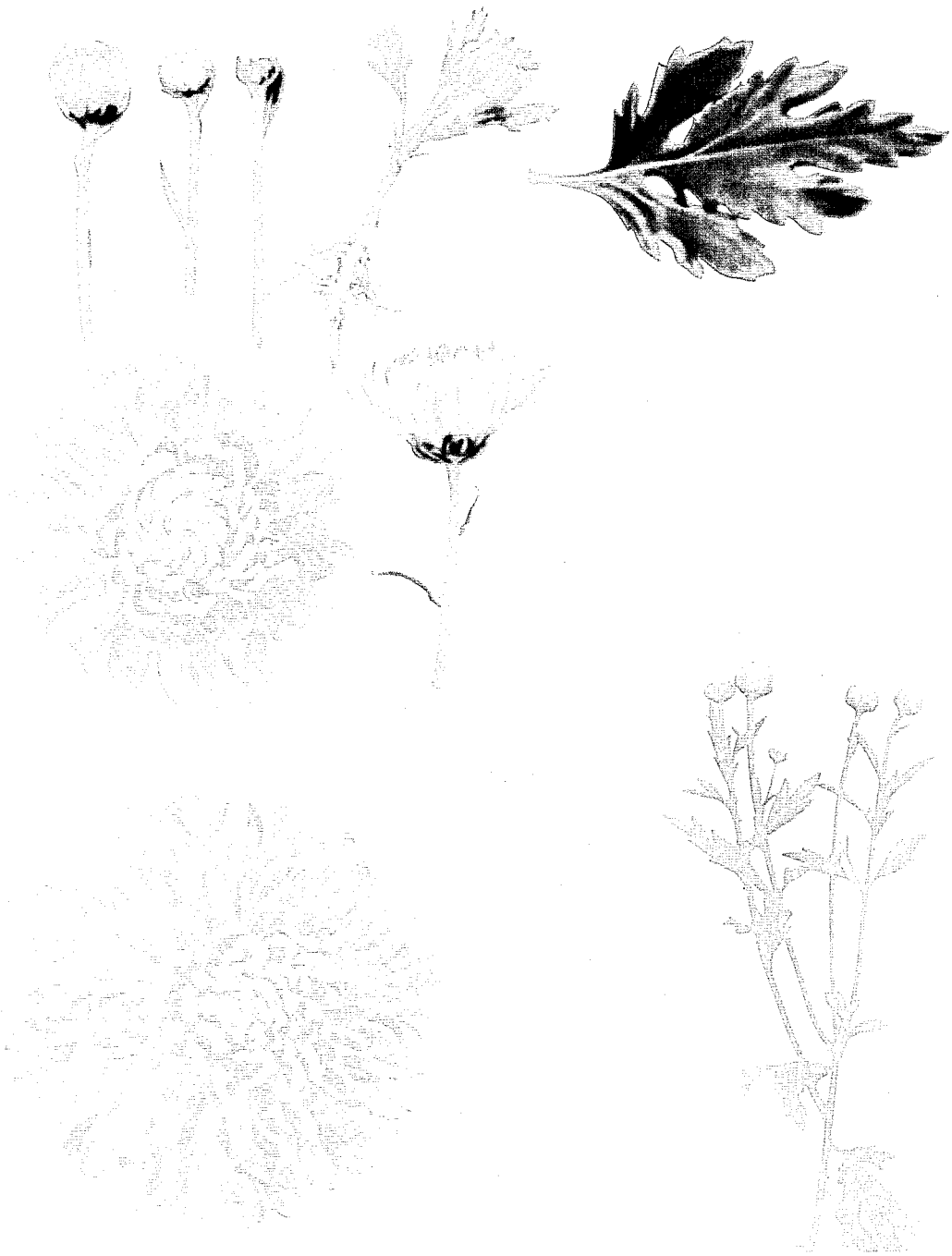
Inventor.
E. S. Boerner
By: Robb & Robb
Attorneys.

United States Patent Office

Plant Pat. 2,739
Patented May 16, 1967

2,739
CHRYSANTHEMUM PLANT

Eugene S. Boerner, Newark, N.Y., assignor to Jackson & Perkins Company, Newark, N.Y., a corporation of New York Filed May 9, 1966, Ser. No. 548,815
1 Claim. (Cl. Plt.—79)

The present invention relates to a new and distinct variety of chrysanthemum plant of the incurved class, which was originated by me by crossing the variety known as "Golden Scepter" (unpatented) with the variety known as "Titmouse," (Plant Patent No. 1,630).

The primary objective of this breeding was to produce a new chrysanthemum variety which bears large flowers of the incurved type comparable to the flowers of the parent variety "Golden Scepter," and combined with the hardiness of frost resistance typical of the parent variety "Titmouse." This objective was fully achieved, among other features, as evidenced by the following unique combination of characteristics which are outstanding in the new variety and distinguish it from its parents, as well as from all other varieties of which I am aware:

(1) Incurved type flowers;
(2) A thick flower form;
(3) A large flower size;
(4) A distinctive and attractive general color tonality of the flowers corresponding to Scarlet, very lightly overcast with Peach Red in the center of the flower petals; and
(5) Good hardiness and frost resistance.

Asexual reproduction of the new variety by both top cuttings and underground runners, as performed at Newark, N.Y., shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black and white for the purpose of illustrating the form and habit of growth of the plant.

The following is a detailed description of the new variety, with color terminology in accordance with Ridgway's Color Standards and Nomenclature:

Parentage: Seedling.
*Seed parent.*—"Golden Scepter."
*Pollen parent.*—"Titmouse."
Classification: Incurved.
Growth: Averages 24 inches tall.
Location where observations made: Outdoors at Newark, N.Y., in the early morning during the early part of the month of October.
Cold Resistance: Winter hardy in northern New York State.

Blooming period: In the Newark, N.Y. climate area, bloom begins in early September and continues until frost.

*Flower*

Bud:
*Color.*—When petals first divide—Coral Red, Plate 13. When petals begin to unfurl—Mustard Yellow, Plate 16, faintly overcast with Antimony Yellow, Plate 15. When half blown: inside—Light Orange-Yellow, Plate 3; outside—Wax Yellow, Plate 16.
*Peduncle.*—Color—Biscay Green, Plate 17. Strength—strong.

Bloom:
*Size.*—5½ inches.
*Stem.*—Stiff.
*Form.*—Incurved and thick.
*Petalage.*—Very double.
*Color.*—Center of flower: inside of petal—Grenadine Red, Plate 2, with lower half of petal overcast with Grenadine, Plate 2; reverse of petal—Pinard Yellow, Plate 4, lightly overcast with Deep Chrome, Plate 3. Outer petals—Salmon Orange, Plate 2, lightly overcast with Coral Red, Plate 13. Base of petals—Deep Chrysolite Green, Plate 31. Inside of petals—Scarlet, Plate 1, very lightly overcast with Peach Red, Plate 1, in the center of the petal. Reverse of petals—Light Orange-Yellow, Plate 3, very lightly overcast with Capucine Buff, Plate 3.
*Petals.*—Texture—medium. Form—oval.
*Fragrance.*—Characteristic chrysanthemum.

*Plant*

Form: Upright.
Growth: Bushy and strong.
Foliage:
*Size.*—Medium.
*Quantity.*—Normal.
*Color.*—Upper side—Deep Dull Yellow Green, Plate 32, Reverse side—Light Bice Green, Plate 17.
*Texture.*—Leathery.

I claim:

A new and distinct variety of chrysanthemum plant of the incurved flower class, substantially as herein shown and described, characterized particularly as to novelty by the unique combination of a habit of bearing flowers of incurved type, a thick flower form, a large flower size, a distinctive and attractive general color tonality of the flowers corresponding to Scarlet, very lightly overcast with Peach Red in the center of the flower petals, and good hardiness and frost resistance.

No references cited.

ABRAHAM G. STONE, *Primary Examiner.*

ROBERT E. BAGWILL, *Examiner.*